US006254865B1

(12) United States Patent
Freed et al.

(10) Patent No.: US 6,254,865 B1
(45) Date of Patent: Jul. 3, 2001

(54) METHOD OF TREATING HUNTINGTON'S DISEASE USING HNT NEURONS

(75) Inventors: Curt R. Freed, Denver; Farida G. Kaddis, Lakewood, both of CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/099,121

(22) Filed: Jun. 17, 1998

Related U.S. Application Data

(60) Provisional application No. 60/049,817, filed on Jun. 17, 1997.

(51) Int. Cl.[7] ................................................ A61K 35/00
(52) U.S. Cl. ........................................ 424/93.7; 424/93.1
(58) Field of Search ................................ 424/93.1, 93.7; 514/44

(56) References Cited

U.S. PATENT DOCUMENTS

| | | |
|---|---|---|
| Re. 35,653 | 11/1997 | Aebischer et al. . |
| 4,353,888 | 10/1982 | Sefton . |
| 4,683,195 | 7/1987 | Mullis et al. . |
| 4,683,202 | 7/1987 | Mullis . |
| 4,744,933 | 5/1988 | Rha et al. . |
| 4,749,620 | 6/1988 | Rha et al. . |
| 4,814,274 | 3/1989 | Shioya et al. . |
| 4,965,188 | 10/1990 | Mullis et al. . |
| 5,084,350 | 1/1992 | Chang et al. . |
| 5,089,272 | 2/1992 | Shioya et al. . |
| 5,175,103 | 12/1992 | Lee et al. . |
| 5,578,442 | 11/1996 | Desai et al. . |
| 5,639,275 | 6/1997 | Baetge et al. . |
| 5,650,148 | 7/1997 | Gage et al. . |
| 5,654,189 | 8/1997 | Lee et al. . |
| 5,676,943 | 10/1997 | Baetge et al. . |
| 5,690,927 | 11/1997 | Major et al. . |
| 5,750,103 | 5/1998 | Cherksey . |
| 5,750,376 | 5/1998 | Weiss et al. . |
| 5,753,491 | 5/1998 | Major et al. . |
| 5,753,505 | 5/1998 | Luskin . |
| 5,792,900 | 8/1998 | Lee et al. . |
| 5,824,489 | 10/1998 | Anderson et al. . |

FOREIGN PATENT DOCUMENTS

| | | |
|---|---|---|
| 301777 | 2/1989 | (EP) . |
| WO 95/12982 | 5/1995 | (WO) . |
| WO 98/34485 | 8/1998 | (WO) . |

OTHER PUBLICATIONS

Cecil Textbook of Medicine, Wyngaarden et al., ed., W.B. Saunders Company, Philadelphia, pp. 2090–2091 and 2147–2148, 1988.*
Jackowski, British J. of Neurosurg., vol. 9, pp. 303–317, 1995.*
Ross et al. Human Gene Therapy, vol. 7, pp. 1781–1790, Sep. 1996.*
Verma et al. Nature, vol. 389, pp. 239–242, Sep. 18, 1997.*
Andrews et al., "Retinoic acid induces neuronal differentiation of a cloned human embryonal carcinoma cell line in vitro," *Develop. Biol.*, 103:285–293 [1984].
Beal et al., "Replication of the neurochemical characteristics of Huntington's disease by quinolinic acid," *Nature* 321:168–171 [1986].
Beal et al., "Differential sparing of somatostatin–neuropeptide Y and cholinergic neurons following striatal excitotoxin lesions," *Synapse* 3:38–47 [1989].
Bjorklund and Stenveni (eds.), *Neural Grafting in the Mammalian CNS*, [1985]; Das, Ch. 3, "Intraparenchymal Transplantation," pp. 23–30; Freed, Ch. 4, "Transplantation of Tissues to the Cerebral Ventricles: Methodological Details and Rate of Graft Survival," pp. 31–40; Stenevi et al., Ch. 5, "Solid Neural Grafts in Intracerebral Transplantation Cavities," pp. 41–50; Brundin et al., Ch. 6, "Intracerebral Grafts of Neuronal Cell Suspensions," pp. 51–60; David et al., Ch. 7, "Peripheral Nerve Transplantation Techniques to Study Axonal Regeneration From the CNS of Adult Mammals," pp. 61–70; and Seiger, Ch. 8, "Preparation of Immature Central Nervous System Regions for Transplantation," pp. 71–77).
Boer et al., "Vasopressin neuron survival in neonatal brattleboro rats; critical factors in graft development and innervation of the host brain," *Neurosci.*, 15:1087–1109 [1985].
Boshart et al., "A very strong enhancer Is located upstream of an immediate early gene of human cytomegalovirus," *Cell* 41:521–530 [1985].
Brundin et al., "Monitoring of cell viability in suspensions of embryonic CNS tissue and its use as a criterion for intercerebral graft survival," *Brain Res.*, 331:251–259 [1985].
Chamberlin et al., "New RNA polymerase from *Escherichia coli* infected with Bacteriophage T7," *Nature* 228:227–231 [1970].
Chen and Okayama, "High–efficiency transformation of mammalian cells by plasmid DNA," *Mol. Cell. Biol.*, 7:2745 [1987].
Concepcion and Low, "Functional heterogeneity of the striatum in a rodent model of Huntington's Disease: consideration for neurological transplantation," *J. Neural Transplant Plast.,*, 3:185 [1992].
Coyle and Schwarcz, "Lesion of striatal neurones with kainic acid provides a model for Huntington's chorea," *Nature* 263:244–246 [1976].

(List continued on next page.)

Primary Examiner—Deborah J. R. Clark
Assistant Examiner—Michael C. Wilson
(74) Attorney, Agent, or Firm—Medlen & Carroll, LLP

(57) ABSTRACT

The present invention relates to methods and compositions for transplantation of neurons. The methods and compositions of the present invention provide a renewable supply of safe and effective therapeutic transplantable tissue. In particular, the present invention provides methods and compositions for the transplantation of terminally differentiated neurons derived from cell lines for the treatment of Huntington's disease and other neurological disorders.

2 Claims, 5 Drawing Sheets

OTHER PUBLICATIONS

Coyle et al., "Neostriatal injections: a model for Huntington's chorea," in *Kainic Acid as a Tool in Neurobiology* (Eds. McGeer et al., Raven Press, New York) Ch.7, pp. 139–159 [1978].

Dale & Federman (eds.) *Scientific American, Medicine*, vol. 3, Ch. 11(XV), pp. 12–13 [1997].

Deckel et al., "Reversal of long–term locomotor abnormalities in the kainic acid model of Huntington's disease by day 18 fetal striatal implants," *Eur. J. Pharmacol.*, 93:287–288 [1983].

Deckel et al., "Receptor characteristics and recovery of function following kainic acid lesions and fetal transplants of the striatum. II. Dopaminergic systems," *Brain Res.*, 474:39–47 [1988].

DePamphilis et al., "Microinjecting DNA into mouse ova to study DNA replication and gene expression and to produce transgenic animals," *BioTechniques* 6:662–680 [1988].

Dijkema et al., "Cloning and expression of the chromosomal immune interferon gene of the rat," *EMBO J.*, 4:761–767 [1985].

Dunnett et al., "Grafts of embryonic substantia nigra reinnervating the ventrolateral striatum ameliorate sensorimotor impairments and akinesia in rats with 6–OHDA lesions of the nigrostriatal pathway," *Brain Res.*, 229:209–217 [1981].

Dunnett et al., "Striatal grafts in rats with unilateral neostriatal lesions—III. Recovery from dopamine–dependent motor asymmetry and deficits in skilled paw reaching," *Neuroscience* 24:813–820 [1988].

Eglitis et al., "Retroviral vectors for introduction of genes into mammalian cells," *BioTechniques* 6:608–612 [1988].

Erlich (ed.), PCR Technology, Stockton Press [1989].

Felgner et al., "Lipofection: a highly efficient, lipid–mediated DNA–transfection procedure," *Proc. Natl. Acad. Sci. USA* 84:7413 [1987].

Fisher and Gage, "Grafting in the mammalian central nervous system," *Physiol. Rev.*, 73:583–616 [1993].

Freed et al., "Transplantation of human fetal dopamine cells for Parkinson's disease," *Arch. Neurol.*, 47:505–512 [1990].

Freed et al., "Survival of implanted fetal dopamine cells and neurologic improvement 12 to 46 months after transplantation for Parkinson's disease," *New Engl. J. Med.*, 327:1549–1555 [1992].

Fricker et al., "The placement of a striatal ibotenic acid lesion affects skilled forelimb use and the direction of drug–induced rotation," *Brain Res. Bull.*, 41:409–416 [1996].

Gage and Fisher, "Intracerebral grafting: a tool for the neurobiologist," *Neuron* 6:1–12 [1991].

Gage, "Fetal implants put to the test," *Nature* 361:405–406 [1993].

Gage, "Cell Therapy," *Nature* 392(Suppl., Apr.):18 [1998].

Gorman et al., "The Rous sarcoma virus long terminal repeat is a strong promoter when introduced into a variety of eukaryotic cells by DNA–mediated transfection," *Proc. Natl. Acad. Sci. USA* 79:6777–6781 [1982].

Graham and van der Eb, "A new technique for the assay of infectivity of human adenovirus 5 DNA," *Virol.*, 52:456–467 [1973].

Gusella et al., "A polymorphic DNA marker genetically linked to Huntington's disease," *Nature* 306:234–238 [1983].

Harper, Huntington's Disease, Eds. W.B. Saunders [1991].

Helm et al., *Exp. Neurol.*, "Development of D1 and D2 Dopamine Receptors and Associated Second Messenger Systems in Fetal Striatal Transplants," 111:181–189 [1991].

Huntington's Disease Collaborative Research Group, "A novel gene containing a trinucleotide repeat that is expanded and unstable on Huntington's disease chromosomes," 72:971–983 [1993].

Isacson et al., "Functional neuronal replacement by grafting striatal neurones in the ibotenic acid–lesioned rat striatum," *Nature* 311:458–460 [1984].

Isacson et al., "Neural grafting in a rat model of Huntington's disease: progressive neurochemical changes after neostriatal ibotenate lesions and striatal tissue grafting," *Neurosci.*, 16:799–817 [1985].

Isacson et al., "Graft–induced behavioral recovery in an animal model of Huntington's disease," *Proc. Natl. Acad. Sci. USA* 83:2728–2732 [1986].

Jilek, In: *Development Neurobiology*, "The reaction and adaptation of the central nervous system to stagnant hypoxia and anoxia during ontogeny," Himwich (ed.), C.C. Thomas Publisher, Springfield, Ill., pp. 331–369 [1970].

Jolly et al., "High–efficiency gene transfer into cells," *Meth. Enzymol.*, 149:10–42 [1987].

Kacian et al., "A replicating RNA molecule suitable for a detailed analysis of extracellular evolution and replication," *Proc. Natl. Acad. Sci. USA* 69:3038–3042 [1972].

Kim et al., "Use of human elongation factor I$\alpha$ promoter as a versatile and efficient expression system." *Gene* 91:217–223 [1990].

Kleppner et al., "Transplanted human neurons derived from a teratocarcinoma cell line (NTera–2) mature, integrate, and survive for over 1 year in the nude mouse brain," *J. Comp. Neurol.*, 357:618–632 [1995].

Leksell and Jernberg, "Stereotaxis and tomography: a technical note," *Acta Neurochir.*, 52:1–7 [1980].

Leksell et al., "A new fixation device for the Leksell stereotaxis system," *J. Neurosurg.*, 66:626–629 [1987].

Lindvall et al., "Grafts of fetal dopamine neurons survive and improve motor function in Parkinson's disease," *Science* 247:574 [1990].

Maniatis et al., "Regulation of Inducible and Tissue–Specific Gene Expression," *Science* 236:1237–1244 [1987].

Maniatis et al., in *Molecular Cloning: A Laboratory Manual*, Cold Spring Harbor Laboratory, N.Y. [1982].

Martin and Gusella, "Huntington's disease—pathogenesis and management," *N. Engl. J. Med.*, 315:1267–1276 [1986].

Mason and Fibiger, "Kainic acid lesions of the striatum: behavioural sequalae similar to Huntington's chorea," *Brain Res.*, 155:313–329 [1978].

Mason and Fibiger, "Kainic acid lesions of the striatum in rats mimic the spontaneous motor abnormalities of Huntington's disease," *Neuropharmacol.*, 18:403–407 [1979].

McCutchan and Pagano, "Enhancement of the infectivity of simian virus 40 deoxyribonucleic acid with diethyl–aminoethyl–dextran," *J. Natl. Cancer Inst.*, 41:351 [1968].

Miller et al., "Generation of Helper–Free Amphotrophic Retroviruses that Transduce a Dominant–Acting, Methotrexate–Resistance Dihydrofolate Reductase Gene," *Mol. Cell. Biol.*, 5:431–437 [1985].

Miller et al., "Redesign of retrovirus packaging cell lines to avoid recombination leading to helper virus production," *Mol. Cell. Biol.*, 6:2895 [1986].

Miyazono et al., "Long–term integration and neuronal differentiation of human embryonal carcinoma cells (NTera–2) transplanted into the caudoputamen of nude mice," *J. Comp. Neurol.*, 376:603–613 [1996].

Mizushima and Nagata, "pEF–BOS, a powerful mammalian expression vector," *Nucl. Acids Res.*, 18:5322 [1990].

Montoya et al. "The "staircase test": a measure of independent forelimb reaching and grasping abilities in rats," *J. Neurosci. Meth.*, 36:219 [1991].

Nieto–Sampedro et al., "The survival of brain transplants is enhanced by extracts from injured brain," *Proc. Natl. Acad. Sci. USA* 81:6250–6254 [1984].

Nieto–Sampedro et al., "Brain injury causes a time–dependent increase in neuronotrophic activity at the lesion site," *Science* 217:860–861 [1982].

Norman et al., "A novel rotational behavior model for assessing the restructuring of striatal dopamine effector systems: are transplants sensitive to peripherally acting drugs?" *Prog. Brain Res.*, 78:61–67 [1988].

Norman et al., "The direction of apomorphine–induced rotation behavior is dependent on the location of excitotoxin lesions in the rat basal ganglia," *Brain Res.*, 569:169–172 [1992].

Philpott te al., "Neuropsychological functioning following fetal striatal transplantation in Huntington's chorea: three case presentations," *Cell Transplan.*, 6:203–212 [1997].

Pleasure and Lee, "NTera 2 cells: a human cell line which displays characteristics expected of a human committed neuronal progenitor cell," *J. Neurosci. Res.*, 35:585–602 [1993].

Richards et al., "Conditioned rotation: a behavioral analysis," *Physiol. Behav.*, 47:1083 [1990].

Richards et al., "Unilateral dopamine depletion causes bilateral deficits in conditioned rotation in rats," *Pharmacol. Biochem. Behav.*, 36:217–223 [1990].

Richards et al., "Trained and amphetamine–induced circling behavior in lesioned, transplanted rats," *J. Neural Trans. Plast.*, 4:157 [1993].

Rosenberg et al., "Grafting genetically modified cells to the damaged brain: restorative effects of NGF expression," *Science* 242:1575 [1988].

Sambrook et al., *Molecular Cloning: A Laboratory Manual*, 2nd ed., Cold Spring Harbor Laboratory Press, New York [1989], pp. 16.6–16.15.

Sanberg et al., "Impaired learning and memory after kainic acid lesions of the striatum: a behavioral model of Huntington's disease," *Brain Res.*, 149:546–551 [1978].

Sanberg and Fibiger, "Body weight, feeding, and drinking behaviors in rats with kainic acid–induced lesions of striatal neurons—with a note on body weight symptomology in Huntington's disease," *Exp. Neurol.*, 66:444–446 [1979].

Schilling et al., "Dominant role of complement in the hyperacute xenograft rejection reaction," *Surg. Gynecol. Obstet.*, 142:29–32 [1976].

Schwarcz et al., "Rotational behaviour in rats with unilateral striatal kainic acid lesions: a behavioural model for studies on intact dopamine receptors," *Brain Res.*, 170:485–495 [1979].

Schwarcz et al., "Quinolinic acid: an endogenous metabolite that produces axon–sparing lesions in rat brain," *Science* 219:316–318 [1983].

Sirinathsinghji et al., "Striatal grafts in rats with unilateral neostriatal lesions—II. In vivo monitoring of GABA release in globus pallidus and substantia nigra," *Neurosci.*, 24:803–811 [1988].

Somogyi et al., "Developmental kinetics of GAD family mRNAs parallel neurogenesis in the rat spinal cord," *J. Neurosci.*, 15:2575–2591 [1995].

Stenevi et al., "Transplantation of central and peripheral monoamine neurons to the adult rat brain: techniques and conditions for survival," *Brain Res.*, 114:1–20 [1976].

Takayama, "Basic fibroblast growth factor increases dopaminergic graft survival and function in a rat model of Parkinson's disease," *Nature Med.*, 1:53–58 [1995].

Toneguzzo et al., "Electric field–mediated DNA transfer: transient and stable gene expression in human and mouse lymphoid cells," *Mol. Cell. Biol.*, 6:703–706 [1986].

Uetsuki et al., "Isolation and characterization of the human chromosomal gene for polypeptide chain elongation factor–1α," *J. Biol. Chem.*, 264:5791–5798 [1989].

Vonsattel et al. "Neuropathological classification of Huntington's disease," *J. Neuropathol. Exp. Neurol.*, 44:559–577 [1985].

Voss et al., "The role of enhancers in the regulation of cell–type–specific transcriptional control," *Trends Biochem. Sci.*, 11:287–289 [1986].

Wishaw et al., "The contributions of motor cortex, nigrostriatal dopamine and cuadate–putamen to skilled forelimb use in the rat," *Brain* 109:805 [1986].

Wolff et al., "Expression of retrovirally transduced genes in primary cultures of adult rat hepatocytes," *Proc. Natl. Acad. Sci. USA* 84:3344 [1987].

Yee et al., Cold Spring Harbor Symp. on Quant. Biol., "Gene expression from a transcriptionally disabled retroviral vector," vol. LI, pp. 1021–1026 [1986].

Trojanowski et al., "Neurons derived from a human teratocarcinoma cell line establish molecular and structural polarity following transplantation into the rodent brain," *Exp. Neurol.*, 122:283–294 [1993].

McKay, "Stem cells in the central nervous system," *Science* 276:66–71 [1997].

Trojanowski et al., "Transfectable and transplantable postmitotic human neurons: a potential "platform" for gene therapy of nervous system diseases," *Exp. Neurol.*, 144:92–97 [1997].

Borlongan et al., "Transplantation of cryopreserved human embryonal carcinoma–derived neurons (NT2N cells) promotes functional recovery in ischemic rats," *Exp. Neurol.*, 149:310–321 [1998].

Dunnett et al., "Neuronal cell transplantation for Parkinson's and Huntington's diseases," *Br. Med. Bull.*, 53(4):757–776 [1997].

Philips et al., "Survival and integration of transplanted postmitotic human neurons following experimental brain injury in immunocompetent rats," *Journal Neurosurg.*, 90:116–124 [1999].

Platt, "New direction for organ transplantation," *Nature* 392(Supp, Apr. 30):11–17 [1998].

Muir et al., "Terminally differentiated human neurons survive and integrate following transplantation into the traumatically injured rat brain," *J. Neurotrauma* 16:403–414 [1999].

Kaddis et al. "Transplantation of hNT neurons into a rat model of Huntington's Disease," The 6th International Neural Transplantation Meeting (Feb. 16, 1999), Poster Presentation Abstract No. SS103, Program p. No. 57.

Hurlbert et al., "Neural transplantation of hNT neurons for Huntington's disease," *Cell Transplant.*, 8:143–151 [1999].

* cited by examiner

A

B

A

B

C

METHOD OF TREATING HUNTINGTON'S DISEASE USING HNT NEURONS

This application claims priority benefit of U.S. provisional application No. 60/049,817, filed Jun. 17, 1997, pending, which is hereby incorporated herein by reference in its entirety.

This invention was made in part during work partially supported by the U.S. National Institute of Health under Grant No. R01 NS18639. The government has certain rights in the invention.

FIELD OF THE INVENTION

The present invention relates to methods and compositions for transplantation of neurons. In particular, the present invention provides methods and compositions for the transplantation of terminally differentiated neurons derived from cell lines for the treatment of Huntington's disease and other neurological disorders.

BACKGROUND OF THE INVENTION

The clinical management of numerous neurological disorders has been frustrated by the progressive nature of degenerative, traumatic, or destructive neurological diseases and the limited efficacy and serious side-effects of available pharmacological agents. Conditions such as Huntington's disease, Alzheimer's disease, severe seizure disorders (e.g., epilepsy and familial dysautonomia), as well as injury or trauma to the nervous system have eluded most conventional pharmacological attempts to alleviate or cure the conditions.

Huntington's disease has proven particularly elusive to conventional pharmacological treatments. Huntington's disease is a progressive degenerative disease of the basal ganglia that is inherited as an autosomal dominant trait. The onset of Huntington's disease, an autosomal dominant, neurodegenerative disorder occurs at an average age of 35 to 40 years but can occur in persons as young as two years old or as old as 80 years (*Scientific American, Medicine*, Dale & Federman, eds. Vol. 3, 11(XV), p. 12–13 [1997]9(IV), p. 29 [1996]). The onset is insidious and is characterized by abnormalities of coordination, movement, and behavior. Movement abnormalities include restlessness, mild postural abnormalities, and quick jerking movements of the fingers, limbs, and trunk. The movement abnormalities may be accompanied by substantial weight loss. Depression is common, and cognitive abnormalities and inappropriate behavior may develop. In contrast to the choreic movements typical of onset in adults, juvenile patients may exhibit rigidity, tremor, and dystonia. In the course of eight to 15 years, the disorder progresses to complete incapacitation, with most patients dying of aspiration pneumonia or inanition.

In 1983, Huntington's disease became the first major inherited disorder with an unidentified basic defect to be linked with a DNA marker (Gusella et al., Nature 306:234 [1983]). The product of this gene, designated huntingtin, contains more than 3000 amino acids and is encoded by 10,366 bases at 4p16.3 (Huntington's Disease Collaborative Research Group, Cell 72:971 [1993]). Although knowledge of the underlying molecular basis for Huntington's disease has increased in recent years, pharmacological treatments based on this molecular knowledge have been limited to alleviating some of the symptoms associated with HD, a procedure that does not address the primary degenerative process nor the nonmotor aspects of the disease.

Cell therapy presents an alternative to these ineffective conventional pharmacological strategies for the treatment of neurological diseases. The goal of cell therapy is to replace, repair, or enhance biological function in damaged or deficient tissues or organs. Cell therapy is accomplished by the transplantation of isolated and characterized cells into a target tissue or organ in sufficient number and quality to restore or impart the desired function. Cell therapy, thus, provides a means of treating disorders where whole or partial organ transplantation is not practical or possible.

Cell transplantation methods have been of particular interest in the treatment of neurological diseases. However, mature neural tissues cannot be used for neural cell transplantation. Such tissues are not capable of surviving or establishing neurological function, which often depends on complex intercellular connections that cannot be surgically established. Thus, it is clear that improved methods and compositions are needed for the effective treatment of neurological diseases.

SUMMARY OF THE INVENTION

The present invention relates to methods and compositions for transplantation of neurons. In particular, the present invention provides methods and compositions for the transplantation of terminally differentiated neurons derived from cell lines for the treatment of Huntington's disease and other neurological disorders. In some embodiments, the present invention provides hNT neurons for transplantation into humans to treat Huntington's disease and other neurological disorders. In other embodiments, the present invention provides animals models for Huntington's disease.

The present invention provides a method for treating defective tissues comprising the steps of: 1) providing a plurality of hNT neurons and a neurologically defective mammal having a target tissue, wherein the target tissue comprises defective cells; and 2) transplanting the plurality of hNT neurons into the mammal under conditions such that a neurological defect of the mammal is ameliorated. In some embodiments, the present invention includes, but is not limited to, encapsulation of the hNT neurons prior to transplantation to reduce immunological response in the host.

In some embodiments, the hNT neurons comprise one or more heterologous nucleic acid sequences. The present invention is not limited to any particular heterologous nucleic acid. Appropriate heterologous nucleic acid sequences include, but are not limited to, nucleic acid sequences encoding a factor useful in ameliorating a defect in the transplant host (e.g., encoding one or more neuropeptide for the treatment of neurological disorders).

In certain embodiments of the present invention, the target tissue of the host comprises tissue of the central nervous system. All tissues of the central nervous system are contemplated by the present invention including, but not limited to, tissues of the brain and spinal cord. In preferred embodiments, the tissue of the central nervous system comprises tissue of the corpus striatum.

In preferred embodiments of the present invention, the host mammal is a human. In other preferred embodiments, the neurological defect comprises a neurological disorder. In particularly preferred embodiments, the neurological disorder is Huntington's disease.

The present invention also provides a method for treating Huntington's disease in a host, comprising transplanting a plurality of hNT neurons into a target tissue of the host. In some embodiments, the hNT neurons comprise one or more heterologous nucleic acid sequences, although the present invention is not limited to hNT neurons that comprises a heterologous nucleic acid sequence. In preferred embodiments of the present invention, the target tissue comprises tissue of the central nervous system. In particularly preferred embodiments, the tissue of the central nervous system comprise tissue of the corpus striatum.

The present invention further provides a non-human mammal having lesions of the corpus striatum and one or more tissues comprising transplanted hNT neurons. In some embodiments, the non-human mammal is selected from the order Rodentia. In particular embodiments, the non-human mammal is selected from the group consisting of mice and rats. In preferred embodiments, the one or more tissues comprising transplanted hNT neurons comprise one or more tissues of the central nervous system. In particularly preferred embodiments, the one or more tissues of the central nervous system comprise tissue of the corpus striatum. In some embodiments, the transplanted hNT neurons comprise one or more heterologous nucleic acid sequences, although the present invention is not limited to hNT neurons that comprise a heterologous nucleic acid sequence.

DESCRIPTION OF THE FIGURES

The file of this patent contains at least one drawing executed in color. Copies of this patent with color drawing (s) will be provided by the Patent and Trademark Office upon request and payment of the necessary fee.

DEFINITIONS

Figure 1:
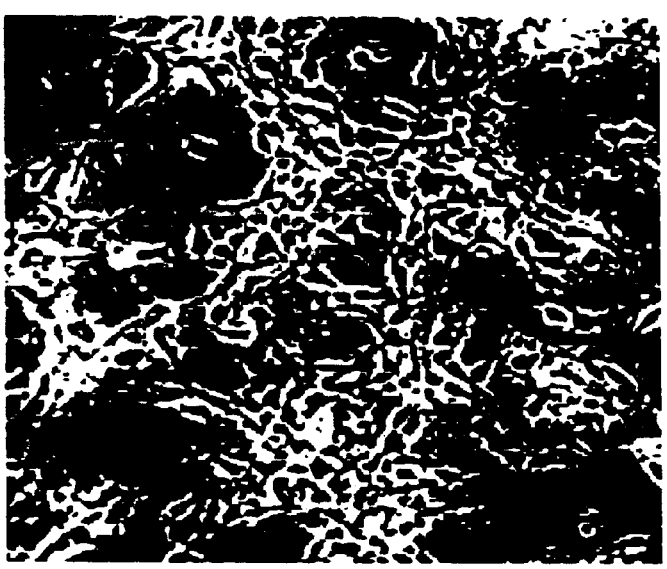
FIG. 1A–B shows: A) hNT neurons on top of a layer of undifferentiated NTera-2 Cells; and B) hNT neurons separated from NT-2 cells and grown on Matrigel coated surface.
Figure 1:
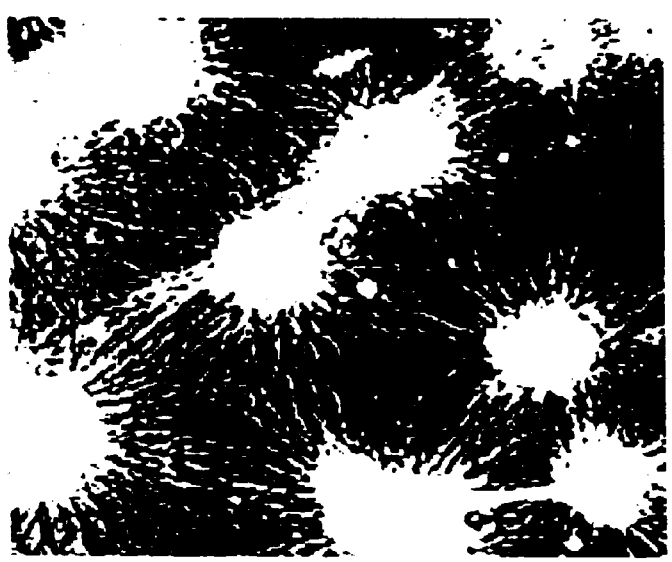

To facilitate an understanding of the present invention, a number of terms and phrases are defined below:

The term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual.

As used herein, the term "stem cell" or "undifferentiated cell" refers to self-renewing cells that are capable of giving rise to phenotypically and genotypically identical daughters as well as at least one other final cell type (e.g., terminally differentiated cells).

As used herein, the term "area postrema" refers to a small elevated area in the lateral wall of the inferior recess of the fourth ventricle; one of the few loci in the brain where the blood-brain barrier is lacking. The term "bregma" refers to the point on the skull corresponding to the junction of the coronal and sagittal sutures. The term "dura" or "dura mater" refers to a tough, fibrous membrane forming the outer covering of the central nervous system. As used herein, the term "dura mater of brain" refers to the intracranial dura mater.

As used herein, the term "central nervous system" refers to all structures within the dura mater. Such structures include, but are not limited to, the brain and spinal cord.

As used herein, the term "host" refers to any warm blooded mammal, including, but not limited to, humans, non-human primates, rodents, and the like, which is to be the recipient of a particular treatment. Typically, the terms "host" and "patient" are used interchangeably herein in reference to a human subject.

As used herein, the terms "defective tissues" and "defective cells" refer to tissues and cells that are marked by subnormal structure, function, or behavior. Defects responsible for the defective tissues and cells include known or detectable defects, as well as, unknown or undetectable defects.

As used herein, the term "neurological defect" refers to a defect involving or relating to the nervous system. Some neurological defects are caused by defective tissues or cells of the nervous system, while other defects are caused by defective tissues or cells that affect the nervous system. As used herein, the term "neurologically defective mammal" refers to a mammal having one or more neurological defects. When a neurological defect is "ameliorated," the condition of the host is improved. For example, amelioration can occur when defective tissue is returned partially or entirely to a normal state. However, amelioration can also occur when tissue remains subnormal, but is otherwise altered to benefit the host.

As used herein, the term "lesion" refers to a wound or injury, or to a pathologic change in a tissue.

As used herein, the term "Huntington's disease" refers to a progressive degenerative disease of the basal ganglia that is inherited as an autosomal dominant trait. Accurate animal models for Huntington's disease can be produced by generating lesions of the striatum and by treating with behavior-inducing agents.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of entire cells, organs, or organisms (e.g., an inhibitor that slows tumor growth).

The term "modulate," as used herein, refers to a change in the biological activity of a biologically active molecule.

Modulation can be an increase or a decrease in activity, a change in binding characteristics, or any other change in the biological, functional, or immunological properties of biologically active molecules.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element which controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "antisense" is used in reference to DNA or RNA sequences that are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook, J. et al., *Molecular Cloning. A Laboratory Manual*, 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue (e.g., tissues of the central nervous system), liquid foods (e.g., milk), and solid foods (e.g., vegetables).

GENERAL DESCRIPTION OF THE INVENTION

The present invention relates to methods and compositions for transplantation of neurons. In particular, the present invention provides methods and compositions for the transplantation of terminally differentiated neurons derived from cell lines for the treatment of Huntington's disease and other neurological disorders.

One common neurological syndrome, Huntington's disease, has been the object of attempts at cell transplant therapy. Huntington's disease (HD) is a genetic neurodegenerative disorder resulting from the expansion of triplet CAG (polyglutamine expansion) in the autosomal dominant IT15 gene, a gene for huntingtin protein (Huntington's Disease Collaborative Research Group, Cell 72:971 [1993]). The disease is characterized by severe neuronal degeneration, primarily in the corpus striatum (caudate nucleus, putamen, and globus pallidus) and, to a lesser extent, degeneration in other brain regions (Vonsattel et al., J. Neuropathology and Experimental Neurology 44:559 [1985]). The symptoms associated with HD include movement abnormalities such as chorea and dystonia, affective disorders, and cognitive impairment. Psychiatric disorders most often present as depression and irritability. The cognitive component of HD is subcortical dementia (Harper, Huntington's Disease, Eds. W. B. Saunders [1991]). In animal models, excitotoxic lesions induced by injection of glutamate receptor agonists into the striatum, mimic the neuronal degeneration observed in HD (Coyle and Schwarcz, Nature 263, 244 [1976]; Sanberg et al., Brain Research 149:546 [1978]; and Sanberg and Fibiger, Experimental Neurology 66:444 [1979]). Thus, animal models provide an effective means for testing methods and compositions for the treatment of Huntington's disease.

Attempts have been made to reverse the clinical manifestations of experimentally-induced Huntington's disease in animals by transplanting fetal brain tissue into the striatum. For example, neural transplants of fetal or newborn striatal tissue have been shown to correct motor deficits and biochemical abnormalities in HD animal models (Deckel et al., Eur. J. Pharmacol 93:287 [1983]; Isacson et al., Nature 311:458 [1984]; Isacson et al., Neuroscience 16:799 [1985]; Dunnett et al., Neuroscience 24:813 [1988]; and Sirinathsinghji et al., Neuroscience 24:803 [1988]). The first clinical studies involving the implanting of fetal tissue into HD human patients are currently underway (See e.g., Philpott et al., Cell Transplantation 6:203 [1997]).

Similar fetal transplantation studies have been conducted for the treatment of Parkinson's disease (PD). Following early, promising results in animals, implantation of fetal brain tissue was used to treat human patients. For example, fetal mesencephalic implants have been efficacious in reducing behavioral deficits in animal models of Parkinson's disease (PD) (Dunnett et al., Brain Research 229:209 [1981]) and have improved symptoms in PD patients (Freed et al., Arch. Neurology 47:505 [1990]; Freed et al., New Engl. J. Med 327:1549 [1992]; and Lindvall et al., Science 247:574 [1990]).

Unfortunately, there are several major limitations to the use of fetal brain tissue for transplantation that render it an insufficient method for treating neurological disorders. Problems with using fetal tissue include social and ethical concerns, as well as the lack of availability of appropriate tissue and variability between specimens. The supply of fetal tissue for cellular transplants is extremely limited and susceptible to government regulatory moratoriums and prohibitions. Compounding the problems of limited tissue supply, to ensure maximum viability, the fetal cells must be freshly harvested prior to transplantation, a procedure that requires coordinating the implantation procedure with elective abortions. Also, the gestational age of the fetus from which the cells are taken influences graft survival (Gage and Fisher, Neuron 6:1 [1991]). Obtaining fetal tissue of only certain gestational ages adds additional limitations to the availability of fetal cells for transplant. In addition to problems in obtaining fetal tissue, some potential transplant recipients are reluctant to undergo a procedure involving fetal cell implantation.

The lack of quality fetal cells makes effective treatment difficult. For example, fetal cell transplantation for treatment of Parkinson's disease has led to limited results because the number of cells that survive in the host brain noticeably affects the functional outcome of the treatment, there is a limited number of cells that can be collected from fetal dissection, and there is variable survival post-transplantation (Gage, Nature 392:18 [1998]). Although strategies to increase the number of fetal cells collected (See e.g., Gage, Nature 361:405 [1993]) and the number of cells surviving in situ (See e.g., Takayama, Nature Med. 1, 53 [1995]) have been attempted, there remains an insufficient amount of transplantable fetal tissue.

Fetal tissue also presents immunological concerns. For example, for allogeneic cells (i.e., cells from the same species as the recipient, but of different genetic origin), the T-cell mediated immune response is of concern (Schilling et al., Surg. Gynecol. Obstet. 142:29 [1976]). Cytoxic T lymphocytes (CTL) are generated to allocell-specific antigens that are expressed with the help of helper T-cells, which are activated by leukocytes. Although the brain has a less complete immunoresponse to foreign cells relative to other tissues (Fisher and Gage, Physiol. Rev. 73:583 [1993]), it is not completely protected from immunological reactivity.

Additionally, because the fetal tissue is obtained from fresh abortuses, some risk of infectious contamination exists (e.g., infection by HSV-1 and/or 2, HIV-1 and/or 2, and HTLV-I and/or II). Although women undergoing abortions that serve as sources of fetal tissue are screened for a variety of infections, some infections such as HIV, may not be clinically detectable and thus, not identified during the screening process.

Because of the many problems and limitations of fetal tissue, there is a dramatic need for alternative sources of transplantable cells. One potential source is xenogeneic cell transplantation (i.e., cells from a different species than the recipient). However, xenogeneic tissue and organ transplants are also ethically controversial, and susceptible to regulatory barriers. Furthermore, in addition to sharing the immunological problems of allografts, xenografts have the potential for more complex immunological issues associated with major histocompatibility complex (MHC) barriers, wherein hyperacute rejection is the rapid and dramatic immunological response. There is also a fear that xenogeneic transplants may transfer new viruses to the human population.

Although more plentiful than fetal tissue, mature neural tissue does not provide an acceptable alternative source for cell transplantation. Mature neural tissue has never been found to survive in transplants (Stenevi et al., Brain Res. 114:1 [1976]). The reason fetal neurons survive grafting procedures while adult neurons do not, while uncertain, is probably due to the fact that fetal neurons are less affected by the low oxygen levels during periods of anoxia than mature neurons (Jilek, In: *Developmental Neurobiology*, Himwich, ed., C. C. Thomas Publisher, Springfield, Ill., pp 331–369 [1970]). It has been reported that fetal neurons survive best when taken during a rapid growth phase and before connections are established with target tissue (i.e., connections present in mature cells)(Boer et al., Neuroscience 15:1087 [1985]), or in the alternative, fetal tissue may be more responsive to growth factors that are present in the damaged host brain (Nieto-Sampedro et al., Science 217:860 [1982]; and Proc. Natl. Acad. Sci. 81:6250 [1984]).

It is clear that the art is in urgent need of methods and compositions for effective and efficient methods and compositions for the treatment of neurological disorders. In particular, a plentiful source of such cells is needed. Ideally, the cells are transplantable without raising serious immunological or ethical concerns and provide effective means to replace, repair, or enhance biological function in damaged or deficient tissues. Methods and compositions for cell transplantation to treat Huntington's disease are particularly needed, since human fetal tissue appropriate for transplant is technically unavailable. The present invention provides the methods and compositions to address these serious needs.

As discussed above, there are significant problems with using fetal tissue for transplantation including social and ethical issues, as well as the lack of availability of appropriate aged tissue and variability between specimens. To circumvent these inherent problems, the present invention provides hNT neurons for the treatment of neurological disorders such as Huntington's disease. hNT neurons, originally derived from a human teratocarcinoma, terminally differentiate into neurons when treated with retinoic acid (Pleasure and Lee, J. Neuroscience Research 35:585 [1993]; and U.S. Pat. No. 5,654,189). The present invention provides methods for the production of these neurons in an unlimited supply, generating transplantable cells that mimic endogenous neuronal tissue and effectively treat neurological disorders. Because the cells can be grown in culture, they are amenable to genetic manipulation prior to transplantation, although the present invention demonstrates that such manipulation is not required for the effectiveness of the neurons. U.S. Pat. No. 5,654,189, herein incorporated by reference in its entirety, describes such methods for gene transfer into undifferentiated NT2 cells, and demonstrated that the cells continue to express proteins encoded by transfected plasmids following differentiation to hNT neurons. Thus, genetic manipulation offers the opportunity to introduce additional functionality (e.g., reduction of host immunological rejection, expression and release of proteins or hormones, etc.) into the transplantable tissue.

Prior to the development of the present invention, there was no immortalized cell line that was shown to be effective in the treatment of Huntington's disease. Although there has been a long-felt need for such a replenishable and reliable source of transplantable tissue, immortalized cell lines for use in transplant therapy are often unacceptable. Many transformed and immortalized cells lose their ability to differentiate fully, and thus can not carry out their unique differentiated cell function (i.e., they are ineffective for cell transplant therapy). Another concern is that immortalized cell lines may cause tumor formation following in vivo transplantation.

Thus, generation of cell lines that can be transplanted for the treatment of neurological diseases requires the development of cells and methods that avoid the risks of tumor formation and severe immunological response and infection, while providing an unlimited source of cells that produce the desired biological functions necessary to treat the patient. Surprisingly, the present invention has overcome these barriers. The present invention provides the first immortalized cell line for the effective treatment of Huntington's disease without significant side-effects, and provides a much needed alternative to the use of fetal tissue.

The safety of hNT transplants was demonstrated by the fact that hNT neurons have survived neurotransplantation for at least one year in nude mice (Kleppner et al., J. Comparative Neurology 357:618 [1995]; and Miyazono et al., J. Comparative Neurology 376:603 [1996]) and for at least three months in primates without tumor formation. Furthermore, the present invention established the effectiveness of hNT transplants by demonstrating that hNT neurons express both GABAergic (i.e., capable of producing γ-aminobutyric acid) and cholinergic (i.e., capable of producing acetylcholine) phenotypes similar to intrinsic striatal neurons and that transplantation of the neurons effectively treated Huntington's disease.

DETAILED DESCRIPTION OF THE INVENTION

The presently claimed invention comprises methods and compositions for transplanting cultured neurons into patients for the treatment of neurological diseases. In one embodiment, the present invention provides methods and compositions for treating a host suffering from a neurological disorder, or alleviating the symptoms of such a disorder, by implanting hNT neurons. Graft rejection, intense intracerebral inflammation, and tumor formation are avoided by the transplantation methods of the present invention. The transplanted neurons are biologically active in the host and produce factors useful in the treatment of neurological diseases such as Huntington's disease.

I. Methods of Treatment

In certain embodiments, the present invention provides means for treating patients with Huntington's disease. Huntington's disease appears to result from the premature death of certain systems of neurons (*Scientific American, Medicine*, Deal & Federman, eds. Volume 3, 11 (XV) p. 12 [1997]). Neurons in various general regions of the brain are selectively vulnerable to cell death, with the most profound degeneration occurring in the corpus striatum (i.e., caudate nucleus and putamen). In addition, specific cell types within the corpus striatum are selectively vulnerable to loss. Medium-sized spiny neurons appear to be the first cells affected. These cells contain the neurotransmitters GABA, substance P, and the enkephalins. The levels of these neurotransmitters are markedly reduced in the brains of patients with Huntington's disease. Large aspiny neurons, which contain acetylcholine, are also affected. Thus, means of elevating these neurotransmitter levels in Huntington's patients should delay or circumvent the progression of the disease. Other aspiny neurons, which contain the peptides somatostatin and neuropeptide Y, as well as the enzyme nicotinamide adenine dinucleotide phosphate diaphorase (NADPH-d), are not significantly affected in Huntington's patients. In fact, concentrations of somatostatin and neuropeptide Y may even increase in patients with Huntington's disease (Martin and Gusella, N. Engl. J. Med. 315:1267 [1986]). Neurons that contain dopamine are also unaffected.

Although knowledge of the neurochemical defects in Huntington's disease has advanced rapidly, effective therapy has not yet been developed. Efforts to relieve symptoms by the administration of precursors or medications that raise the levels of acetylcholine or GABA in the brain have failed.

In one embodiment of the present invention, hNT neurons are transplanted into the central nervous system of Huntington's disease patients. hNT neurons produce both GABAergic and cholinergic phenotypes, providing the host with a source of neurotransmitters that are lacking in the tissues.

As described herein, the effectiveness of hNT neurons using the present invention for treating neurological disorders has been demonstrated in animal models of Huntington's disease. In certain embodiments, animal models for HD were produced by generating lesions of the striatum and by treating with behavior-inducing agents. For example, in rodents, excitotoxic lesions induced by kainic acid or ibotenic acid cause extensive loss of neurons in the injected area (Coyle and Schwarcz, Nature 263:244 [1976]; Sanberg et al., Brain Research 149:546 [1978], Sanberg and Fibiger, Experimental Neurology 66:444 [1979]; Coyle et al, Kainic Acid as a Tool in Neurobiology 7:139 [1978]; Mason and Fibiger, Brain Research 155:313 [1978]; and Mason and Fibiger, Neuropharmacology 18:403 [1979]). More recently, it has been shown that the same selectivity of striatal cell loss that is found in Huntington's disease may be produced in rats by intrastriatal injection of quinolinic acid (QA), an excitatory compound that is a naturally occurring metabolite of tryptophan (Beal et al., Nature 321:168 [1986]). Interestingly, quinolinic acid treatment spares subsets of neurons, such as NADPH diaphorase, somatostatin, and neuropeptide Y positive neurons (Schwarcz et al., Science 219:316 [1983]; and Beal et al., Synapse 3:38 [1989]). Thus, animal models treated with quinolinic acid provide a remarkably accurate model of human HD.

Unilateral excitotoxic lesions of the striatum cause a dopamine-dependent circling behavior. Thus, systemic administration of dopaminergic agents such as apomorphine or methamphetamine results in circling behavior ipsilateral to the lesioned side (Dunnett et al, Neuroscience 24:813 [1988]; and Schwarcz et al., Brain Research 170:485 [1979]). The location of more restricted unilateral striatal lesions results in varied behavioral responses to apomorphine. In contrast, with a lesion limited to anteromedial striatum, apomorphine leads to circling contralateral to the lesion side (Norman et al., Brain Research 569:169 [1992]; Norman et al., Prog. Brain Res. 78:61 [1988]; and Concepcion and Low, J. Neural Transplant Plast. 3:185 (1992]). In addition to the dopamine-dependent circling behavior, unilateral lesions yield deficits in skilled use of the paw contralateral to the lesion side as determined in the staircase test (Montoya et al, J. Neuroscience Methods 36:219 [1991]; and Wishaw et al., Brain 109:805 [1986]). In one embodiment of the present invention, a relatively large, posterior QA-induced lesion of caudate putamen was induced to produce neuronal degeneration similar to HD, unambiguous ipsilateral circling to dopamine agonists, and skilled motor deficits in the contralateral paw. However, it was found that larger lesions were necessary to produce circling behavior in response to apomorphine and methamphetamine. Thus, in other embodiments, larger lesions are produced so that the animals exhibit the desired behavior.

Figure 3:
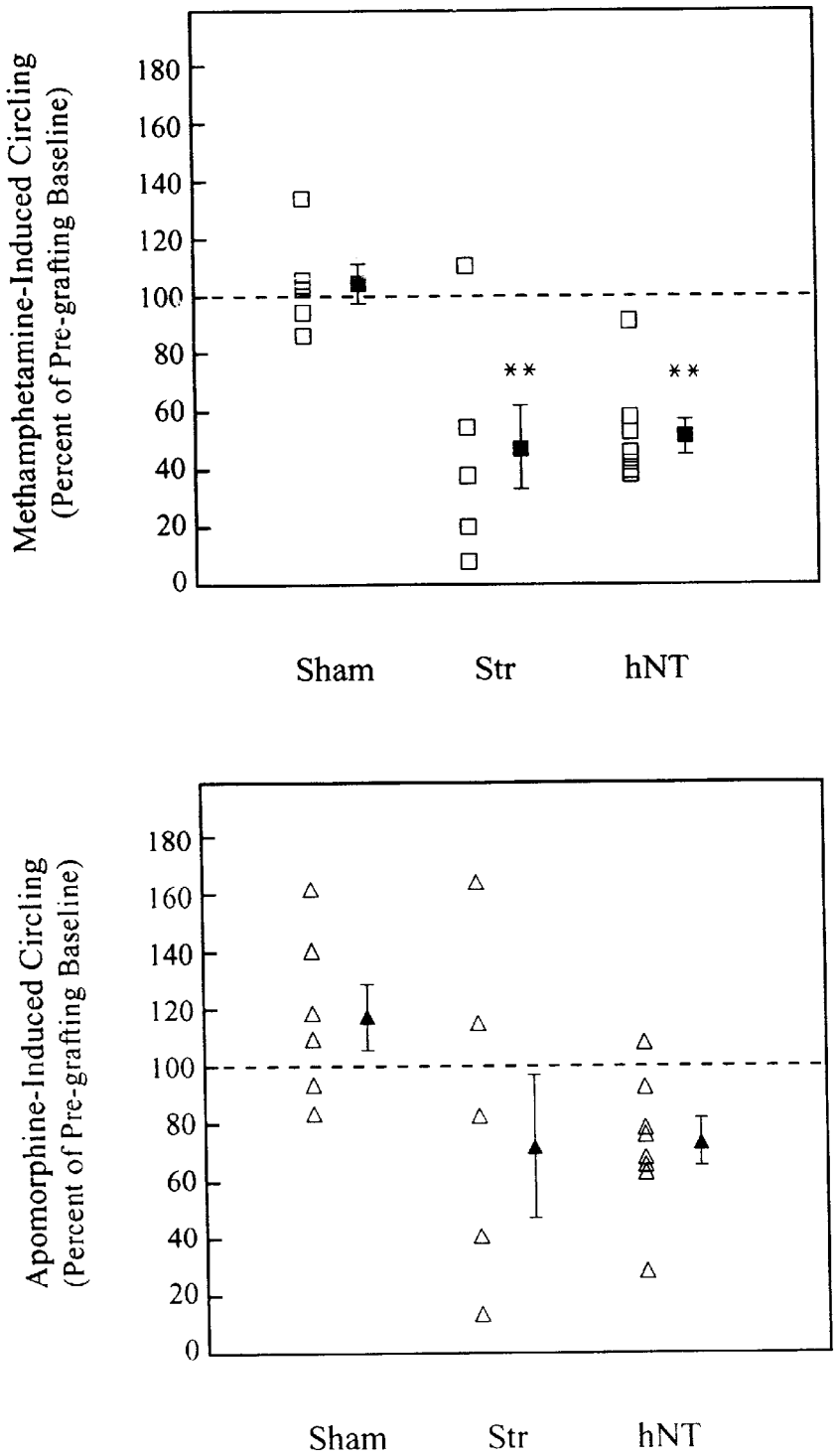
FIG. 3 shows data representing dopamine-dependent motor asymmetry in animals with unilateral striatal lesions as measured by circling behavior in response to methamphetamine (top diagram) or apomorphine (bottom diagram).

In one embodiment of the present invention, transplantation of hNT neurons to these lesioned animals resulted in improved physical performance. Quinolinic acid-induced lesions of the striatum resulted in circling ipsilateral to the lesion in response to methamphetamine (5.0 mg/kg) and apomorphine (1.0 mg/kg). Intrastriatal grafts of either embryonic striatal tissue or hNT neurons resulted in a gradual reduction in drug-induced circling behavior. At 12 weeks post-transplantation, methamphetamine-induced circling behavior was reduced to 50% of pre-grafting baseline of the animals grafted with fetal striatal tissue and to 56% for the hNT neuron transplanted animals (p<0.01, Student-Newman-Keuls), as shown in the top of FIG. 3. As indicated in this figure, animals transplanted with hNT neurons (hNT, n=8) or fetal striatal tissue (Str, n=6), demonstrated reduction in circling behavior, while sham transplant animals (Sham, n=6) showed no significant change in circling behavior. In FIG. 3, individual animals are represented by open symbols, with group averages represented by closed symbols. Also, as shown in the bottom panel of FIG. 3, the apomorphine-induced ipsilateral circling was reduced to 63% and 65% of pre-transplantation baseline in the fetal striatal tissue and hNT neuron grafted animals, respectively (data not statistically different from controls). Control animals (Sham) showed no improvement on circling behavior induced by either apomorphine or methamphetamine.

Figure 4:
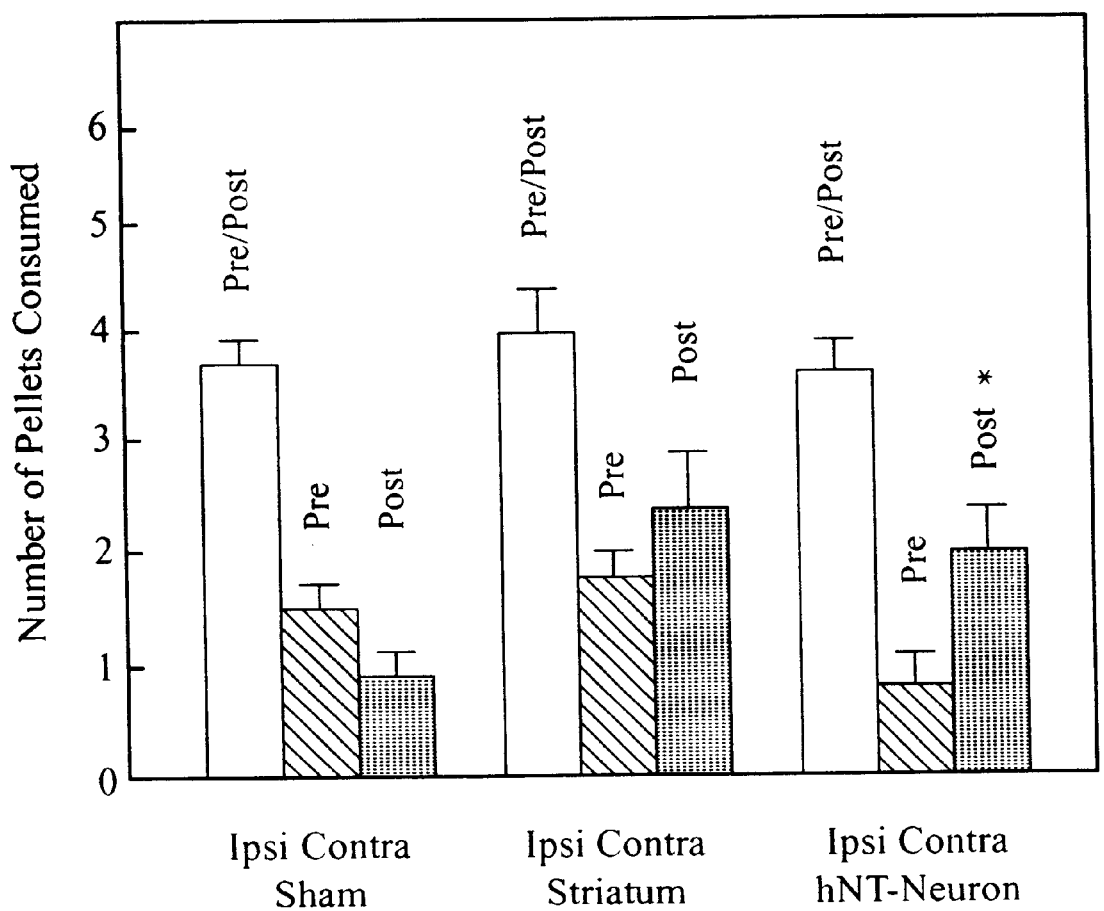
FIG. 4 shows data representing skilled motor use of paws by animals with and without hNT neuron transplantation in the stair case test.

In the staircase test for skilled paw use, all lesioned animals showed deficits in use of the paw contralateral to the side of lesion prior to transplantation as determined by successful eating attempts averaged from 15 minute test intervals in the stair case apparatus, over 15 days of behavioral testing. The mean value for the deficit in the use of the paw contralateral to the lesioned side compared to ipsilateral paw use was 77%, 55%, and 59% in the animals transplanted with hNT neurons, fetal striatal tissues or sham, respectively, as shown in FIG. 4. At 10 weeks post-transplantation, these values were improved to 43% (p<0.028, two-tailed Student's t-test) and 41% (statistically not different) for animals that received grafts of hNT neurons and fetal striatal tissue, respectively, as shown in FIG. 4. In contrast, sham transplanted animals showed continued deterioration in use of the paw contralateral to the lesioned side from a 59% to a 76% deficit compared to the ipsilateral paw (FIG. 4).

Figure 5:
FIG. 5A–C shows micrographs of coronal sections of rat brains treated with: A) hNT neurons; B) fetal striatal (ED15) cells; and C) sham transplants.
Figure 5:
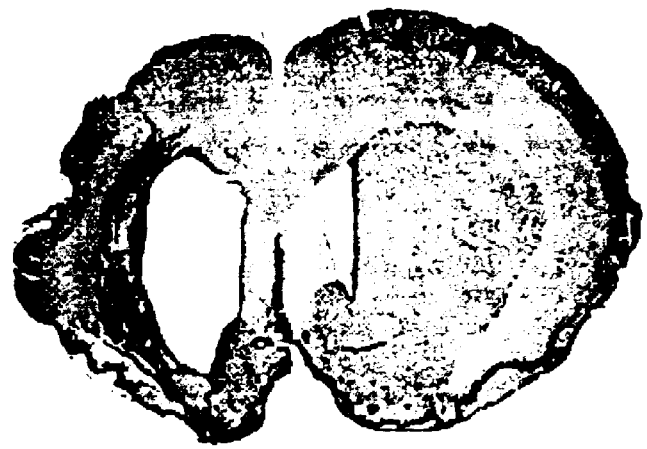
Figure 5:

The extent of the lesion induced by QA injection was determined in all animals by histochemical analysis. Consecutive sections, starting from the first appearance of the lesion-induced tissue loss until the end of the lesion, were histochemically stained for Nissl bodies. Analysis revealed that QA induced a massive loss of the corpus striatum, as shown in FIG. 5A, B, and C, showing micrographs of coronal sections (40 μm) of rat brains.

In many animals, the lesion also extended to the cortex (frontal and/or temporal). Despite this severe lesion, target nuclei of striatal efferents, namely globus pallidus and the substantia nigra, were preserved. The medial transplant tract was not placed into the brain parenchyma due to the enlarged ventricle and did not survive. The transplanted hNT neurons were not immunoreactive for DARPP-32, a striatal cell marker, while the transplanted fetal striatal neurons were immunoreactive. Staining of neurons for Nissl substance allowed for easy recognition of the surviving hNT neurons transplanted at the more lateral site, as seen in FIG. 5A. The volume of the fetal striatal tissue transplant was 5.0 fold larger than the volume of hNT grafts as estimated by assembling the surface areas of scanned consecutive coronal brain sections (FIGS. 5A and B).

The time course of behavioral recovery observed using the methods of the present invention is similar to previous reports using fetal cell transplants in HD animal models. Both hNT neurons and fetal striatal cell transplants require 8 to 12 weeks to show behavioral effects, suggesting that the hNT neurons, like embryonic striatal cells, require neural connectivity prior to behavioral recovery. At 10 weeks post-transplantation in animals with unilateral lesions, transplantation of ED13–15 fetal striatal cell suspensions showed functional recovery of the lesion-induced hypermetabolic responses, as measured by 2-deoxy[$^{14}$C]glucose (Isacson et al., Nature 311:458 [1984]). In rats with bilateral ibotenic acid lesions, overnight locomotor hyperactivity was completely compensated for by intrastriatal fetal striatal implants at 10–15 weeks post-transplantation (Isacson et al., Proc. Natl. Acad. Sci. 83:2728 [1986]). In a longer term study, Dunnett, et al. (Dunnett et al., Neuroscience 24:813 [1988]), showed progressive reduction in both methamphetamine and apomorphine-induced circling and greater recovery in skilled use of both paws in the staircase test at seven months post-transplantation of embryonic striatal tissue. It is contemplated that longer follow-up of animals with hNT neural transplants will produce even greater behavioral improvement. Nonetheless, the present invention provides methods and compositions, in particular hNT neurons, that are a useful alternative to fetal striatal tissue for neural transplantation treatment of Huntington's disease. Thus, the present invention provides many advantages (e.g., a renewable cell source that can be tailored for desired functionality) over the prior methods and compositions for the treatment of Huntington's disease.

It is also contemplated that the methods and compositions of the present invention will find use in the treatment of other neurological disorders including, but not limited to, Parkinson's disease, Alzheimer's disease, multiple sclerosis, amyotrophic lateral sclerosis, Gaucher's disease, Tay-Sachs disease, neuropathies, and brain tumors, among others. As the hNT neurons transplanted by the methods of the present invention are compatible with the central nervous system, these cells can also be transfected with DNA sequences encoding physiologically active peptides, and implanted in the central nervous system to effect treatment of other disorders. For example, for treatment of multiple sclerosis, it is contemplated that hNT neurons are adapted to express a trophic stimulator of myelination, such as platelet derived growth factor or a ciliary trophic factor that may block oligodendrocyte degeneration. Because multiple sclerosis is more generalized than local lesions, alternative implantation methods may be desirable. For example, it is contemplated that the cells be implanted on a surface exposed to cerebrospinal fluid. Following expression and secretion, the expressed peptide washes over the entire surface of the brain by the natural circulation of the cerebrospinal fluid. In treatment of Alzheimer's disease it is contemplated that the hNT neurons are transfected to produce nerve growth factor to support neurons of the basal forebrain as described by Rosenberk et al. (Rosenberk et al, Science 242:1575 [1988]).

For treatment of Parkinson's disease, it is contemplated that hNT neurons be adapted to express tyrosine hydroxylase (i.e., the enzyme that converts tyrosine to L-DOPA). Expression of tyrosine hydroxylase by the implanted cells allows these cells to produce and secrete dopamine, potentially increasing the dopamine concentration in the substantia nigra and limiting or reversing the effect of dopaminergic neuron loss.

It is also contemplated that the hNT neurons of the present invention be genetically modified to produce a desired neurological factor for the treatment of a range of diseases and disorders. Furthermore, it is contemplated that hNT neurons will find use in the treatment of non-neurological diseases. As the cells have been shown to be transplantable and to survive in the host for an extended period, they can be used to deliver at least one peptide of interest for any desired purpose.

II. hNT Neurons

Figure 2:
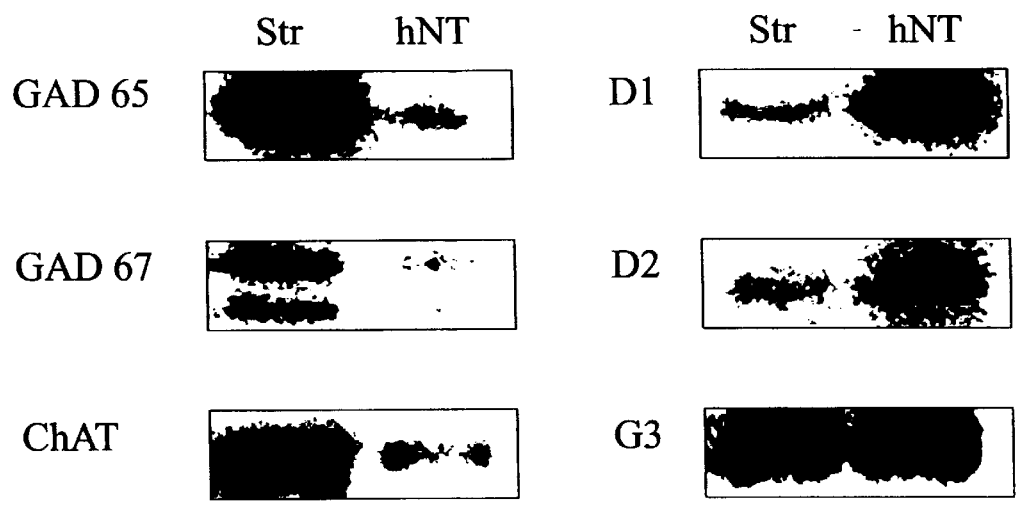
FIG. 2 shows the detection of neuronal phenotypes in hNT neurons and human fetal striatal tissue as determined by RT-PCR.

The similarities in neurochemical phenotype of hNT neurons and fetal striatal tissue are substantial. Although an understanding of the mechanism is not necessary in order to use the present invention, it is likely that these characteristics result in the behavioral recovery that is similar to that observed with transplantation of embryonic striatal tissue. The present invention provides hNT neurons that have the synthetic enzymes to make GABA and acetylcholine. In addition, the hNT neurons express D1 and D2 dopamine receptors. Although an understanding of the mechanism is not necessary in order to use the present invention, it is hypothesized that the D1 and D2 dopamine receptors may be important because others have found expression of these receptors was necessary for behavioral recovery (Deckel et al., Brain Research 474:39 [1988]; and Helm et al., Experimental Neurology 111:181 [1991]). On the other hand, it was found that hNT neurons fail to express DARPP-32, as shown by lack of immunostaining with the DARPP-32 antibody. This result demonstrates that the hNT cells are not identical to striatal neurons, and, along with the many complications and drawbacks of using immortalized cells for transplantation, made it unclear whether hNT cells could provide effective transplantable tissue for treating neurological diseases.

hNT neurons were obtained by differentiating NT2 cells as described in Example 1 and U.S. Pat. No. 5,654,189, herein incorporated by reference. Once differentiated, the hNT neurons were collected and used in transplantation therapy. The differentiated hNT neurons were characterized to determine their capability to produce neurotransmitters and other important factors. RT-PCR showed that differentiated hNT neurons and human embryonic striatum express mRNA for enzymes in the synthetic pathways of the neurotransmitters GABA and acetylcholine. It was found that both hNT neurons and human fetal striatal tissue express choline acetyltransferase (ChAT) and two isoforms of glutamic acid decarboxylase, GAD65 and GAD67. FIG. 2 shows 6–8 week post-gestation human striatal tissue (Str) and hNT neurons (hNT) mRNA expression patterns. Additionally, as shown in FIG. 2, the fetal striatal tissue and hNT neurons express mRNA for both $D_1$ and $D_2$ dopamine receptors. In this figure, G3PDH (G3) is shown as a control RNA. The double bands seen in the GAD67 PCR products represent alternatively spliced transcripts, GAD67 and EP10, both of which code for functional glutamic acid decarboxylase (Somogyi et al., J. Neuroscience 15:2575 [1995]). As shown, the hNT neurons appear to express higher levels of $D_1$ and $D_2$ dopamine receptor mRNA than the human fetal striatal tissue tested in these experiments. These results demonstrate that hNT neurons are capable of producing neurotransmitters, useful for the treatment of neurological diseases, without requiring the transgenic addition of such functionalities.

In alternative embodiments, the hNT neurons are transfected with nucleic acid that encodes at least one important neurological factor. Such factors include, but are not limited to, naturally occurring neural peptides, proteins, or enzymes, or may be peptide or protein fragments that have therapeutic activity within the central nervous system. Examples include neuronal growth factors and enzymes used to catalyze the production of important neuro-chemicals, or their intermediates.

In other embodiments, the cells are transfected with, and capable of expressing, heterologous nucleic acid sequence that encodes at least one desired neurological factor. As used herein, the term "heterologous nucleic acid" refers to a non-naturally occurring nucleic acid within the cell line transfected with the sequence. Thus, in some embodiments, the heterologous sequence comprises a segment that is entirely foreign to the cell line, or alternatively (i.e., in other embodiments), comprises a native segment that is incorporated within the cell line in a non-native fashion (e.g., linked to a non-native promoter/enhancer sequence, linked to a native promoter that is not typically associated with the segment, or provided in multiple copies where the cell line normally provides one or no copies).

It is also contemplated that in some embodiments, the peptide encoded by the nucleic acid is a therapeutic compound (e.g., a movement inhibitor for the treatment of Huntington's disease). In alternative embodiments, the peptide encoded by the nucleic acid is selected to supplement or replace deficient production of the peptide by the endogenous tissues of the host, the deficiency of which contributes to or causes the symptoms of a particular disorder. In this case, the cell lines act as an artificial source of the peptide.

Methods for transfecting hNT neurons are taught by U.S. Pat. No. 5,654,189, and described in Example 7. One skilled in the art is capable of practicing such techniques using methods standard in the art. However, a brief description of such techniques is provided for convenience.

As a general strategy, the following steps can be taken when designing genetically altered transplantable hNT neurons: 1) selection of an appropriate transgene or transgenes whose expression is correlated with a desired biological activity (e.g., correlated with a neurological dysfunction); 2) selection and development of suitable and efficient vectors for gene transfer; 3) preparation of transfectable hNT precursor cells; 4) gene transfer; 5) demonstration that the donor implanted cells expressing the new function are viable and can express the transgene product(s) stably and efficiently; 6) demonstration that the transplantation causes no serious deleterious effects; and 7) demonstration of a desired phenotypic effect in the host animal. However, it is not intended that the present invention be limited to this particular strategy. Indeed, it is intended that any appropriate approach be used, as indicated by the patient's disease.

In some embodiments, preferred vectors for use in the methods of the present invention are viral, including retroviral, vectors. The viral vector selected should meet the following criteria: 1) the vector must be able to infect the donor cells and, thus, viral vectors having an appropriate host range must be selected; 2) the transferred gene should be capable of persisting and being expressed in a cell for an extended period of time without causing cell death for stable maintenance and expression in the cell; and 3) the vector should do little, if any, damage to target cells. Murine retroviral vectors offer an efficient, useful, and well-characterized means of efficiently introducing and expressing foreign genes in mammalian cells. These vectors have very broad host and cell type ranges, integrate by well understood mechanisms into random sites in the host genome, express genes stably and efficiently, and under most conditions, do not kill or obviously damage their host cells.

Construction of suitable vectors containing the desired gene coding and control sequences employs standard ligation and restriction techniques, which are well understood in the art (See e.g., Maniatis et al., in *Molecular Cloning: A Laboratory Manual*, Cold Spring Harbor Laboratory, N.Y. [1982]). Isolated plasmids, DNA sequences, or synthesized oligonucleotides are cleaved, tailored, and religated in the form desired. In addition, methods of preparation of retroviral vectors have been described (See e.g., Yee et al., *Cold Spring Harbor Symp. on Quant. Biol.* Vol. LI, pp. 1021–1026 [1986]; Wolff et al., Proc. Natl. Acad. Sci. 84:3344 [1987]; Jolly et al., Meth. in Enzymol. 149:10 [1987]; Miller et al., Mol. Cell. Biol. 5:431 [1985]; Miller et al., Mol. Cell. Biol. 6:2895 [1986]; and Eglitis et al., Biotechniques 6: 608 [1988]).

It is contemplated that other viral vectors will find use with the present invention including, but not limited to, papovaviruses (e.g., JC, SV40, polyoma, and adenoviruses), Epstein-Barr Virus, papilloma viruses, vaccinia and poliovirus, among other native or modified human and animal viruses.

In addition to the above-described methods for inserting functional transgenes into donor cells, other non-viral methods can be used including, but not limited to, microinjection (See e.g., DePamphilis et al., BioTechniques 6:662 [1988]); electroporation (See e.g. Toneguzzo et al., Mol. Cell. Biol. 6:703 [1986]); chemically mediated transfection (e.g., calcium phosphate transfection [See e.g., Chen and Okayama, Mol. Cell. Biol. 7:2745 (1987)] and DEAE-dextran mediated transfer [See e.g., McCutchan and Pagano, J. Natl. Cancer Inst. 41:351 (1968)]; and cationic liposomal mediated transfection (See e.g., Felgner et al., Proc. Natl. Acad. Sci. 84:7413 [1987]; among other methods known in the art.

III. Transplantation

It is contemplated that in most embodiments of the present invention that the viability of the cells to be transplanted will be assessed. In one embodiment, the cells are assayed as described by Brundin et al (Brundin et al., Brain Res., 331:251 [1985]), although any means of determining the quality of the cells is contemplated by the present invention. In the Brundin et al. method, sample aliquots of the cell suspension to be transplanted (1–4 $\mu$l) are mixed on a glass slide with 10 $\mu$l of a mixture of acridine orange and ethidium bromide (3.4 $\mu$g/ml of each component in 0.9% saline; Sigma). The suspension is transferred to a hemocytometer, and viable and non-viable cells are visually counted using a fluorescence microscope under epi-illumination at 390 nm combined with white light trans-illumination to visualize the counting chamber grid. Acridine orange stains live nuclei green, whereas ethidium bromide will enter dead cells resulting in orange-red fluorescence. In order to facilitate successful transplantation, these cell suspensions should generally contain more than about 98% viable cells.

For implantation of the cells into the brain, stereotaxic methods are generally used (See e.g., Leksell and Jernberg, Acta Neurochir. 52:1 [1980]; and Leksell et al., J. Neurosurg. 66:626 [1987]). Methods for transplanting cells to specific regions of the central nervous system are taught by U.S. Pat. No. 5,650,148, incorporated herein by reference. These neural transplantation or "grafting" methods involve transplantation of cells into the central nervous system or into the ventricular cavities or subdurally onto the surface of a host brain. Considerations for successful transplantation include: 1) viability of the implant; 2) retention of the graft at the site of transplantation; and 3) minimum amount of pathological reaction at the site of transplantation.

Methods for transplanting various nerve tissues have been described in *Neural Grafting in the Mammalian CNS*, (Bjorklund and Stenveni, eds. [1985]); Das, Ch. 3 pp. 23–30; Freed Ch. 4, pp. 31–40; Stenevi et al., Ch. 5, pp. 41–50; Brundin et al., Ch. 6, pp. 51–60; David et al., Ch. 7, pp. 61–70; and Seiger, Ch. 8, pp. 71–77), herein incorporated by reference. In some grafting embodiments, the cell suspension is drawn up into a syringe and administered to anesthetized graft recipients. Multiple injections may be made using this procedure.

The use of such cellular suspension procedures provides many advantages. For example, these methods permit grafting cells to any predetermined site in the brain or spinal cord, are relatively non-traumatic, allow multiple grafting simultaneously in several different sites or the same site using the same cell suspension, and permit the use of mixed cells obtained from different anatomical regions. Preferably, from approximately $10^4$ to approximately $10^8$ cells are introduced per graft, although certain applications may require higher or lower numbers.

Typically, the number of cells transplanted into the patient or host will be a "therapeutically effective amount." As used herein, "therapeutically effective amount" refers to the number of transplanted cells that are required to effect treatment of the particular disorder for which treatment is sought. For example, where the treatment is for Huntington's disease, transplantation of therapeutically effective amount of cells will typically produce a reduction in the amount and/or severity of the symptoms associated with Huntington's disease. Persons of skill in the art will understand how to determine proper cell dosages.

In some embodiments, it may be desired that the hNT neurons be treated prior to transplantation in order to reduce the risk of stimulating host immunological response against the transplanted hNT neurons. For example, in some embodiments, the cells are encapsulated by membranes prior to implantation. The encapsulation provides a barrier to the host's immune system and inhibits graft rejection and inflammation. It is contemplated that any of the many methods of cell encapsulation available will be employed. In some instances, cells are individually encapsulated. In other instances, many cells are encapsulated within the same membrane. In embodiments in which the cells are removed following implantation, the relatively large size of a structure encapsulating many cells within a single membrane provides a convenient means for retrieval of the implanted cells. Several methods of cell encapsulation are well known in the art, such as those described in European Patent Publication No. 301,777 or U.S. Pat. Nos. 4,353,888; 4,744,933; 4,749,620; 4,814,274; 5,084,350; 5,089,272; 5,578,442; 5,639,275; and 5,676,943, each of which is incorporated herein by reference.

EXPERIMENTAL

The following examples are provided in order to demonstrate and further illustrate certain preferred embodiments and aspects of the present invention and are not to be construed as limiting the scope thereof. Most of the techniques used to transform cells, construct vectors, and the like are widely practiced in the art, and most practitioners are familiar with the standard resource materials that describe specific conditions and procedures. However, for convenience, the following descriptions may serve as guidelines.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); i.p. (intraperitoneally); s.c. (subcutaneously); I.D. (interior diameter); AP (anterior/posterior); L (lateral); V (vertical); Sigma (Sigma Chemical Co., St. Louis, Mo.); and Biorad (Bio-Rad Laboratories, Hercules, Calif.).

EXAMPLE 1

Cell Culture

NT2 cells were maintained in DMEM (high glucose) including 10% fetal bovine serum and penicillin/streptomycin, as previously described (Andrews et al., Developmental Biology 103:285 [1984]). For differentiation, $2 \times 10^6$ cells were seeded into a 75 cm$^2$ flask and treated with $1 \times 10^{-2}$ M retinoic acid (RA) (a $1 \times 10^{-2}$ M stock dissolved in DMSO was prepared fresh monthly) twice a week for four weeks. Following RA treatment, the cells were passaged at 1:6. After two days, cells were mechanically dislodged (i.e., culture flasks were struck ten times on each side). The floating cells were washed with 5 ml of medium and replated again on diluted Matrigel (Collaborative Biomedical Research, MA), 1:20 Matrigel dilution for coverslips or 1:60 for dishes, following the manufacturer's instructions (the dilutions used for the Matrigel varied somewhat from lot to lot). Cells were seeded at a density of $0.2 \times 10^6$ cells per 12 mm coverslip or $7.5 \times 10^6$ cells per 100 mm dish in DMEM with 10% serum and penicillin/streptomycin.

EXAMPLE 2

In Vitro Characterization of hNT Neurons hNT neurons were differentiated and characterized to assess neurotransmitter phenotypes. hNT neurons were cultured in DMEM supplemented with 10% FBS. Cells were differentiated by exposure to 10 µM retinoic acid (RA) for 5 weeks. Following RA treatment, cells were passaged 1:6 and treated for 7 days with a mixture of antimitotic agents (1 µM cytosine arabinoside, 10 µM fluorodeoxyuridine, and 10 µM uridine). Differentiated hNT neurons were then separated from the underlying undifferentiated cell layer. FIG. 1A shows differentiated hNT neurons on top of a layer of undifferentiated NTera-2 Cells. FIG. 1B shows hNT neurons following separation from NT-2 cells and grown on matrigel coated surface.

To assess neurotransmitter phenotype by RT-PCR, total RNA was collected from purified hNT neurons in culture or from freshly dissected human fetal striatum (6 to 8 weeks post conception) using RNeasy Total RNA isolation kit (Qiagen, Chatsworth Calif.). Human fetal tissue was obtained from elective abortions with women giving informed consent to scientific use of the tissue. State and Federal laws were followed. Following collection of tissue, 1 µg of total RNA was reverse transcribed (RT) using MulV reverse transcriptase (Perkin-Elmer). One tenth of the RT reaction was used as a template in the polymerase chain reaction (PCR). The conditions for the PCR were as follows: denaturation (96° C., 40 seconds), annealing (60° C., 40 seconds), and elongation (72° C., 60 seconds), 25 cycles, using a Perkin-Elmer 9600 Cycler. A trace amount of [α-$^{32}$P]dCTP (1.5 µCi) was added to each of the reactions. The primers used in the PCR were as follows: hGAD65, forward primer (F) 5'-GGCTCTGGCTTTTGGTCTTTC-3' (SEQ ID NO:1); reverse primer (R) 5'-TGCCAATTCCCAATTATATTCTTGG-3' (SEQ ID NO:2); hGAD67, forward primer (F) 5'-GCTGGAAGGCATGGAGGGCTTCA-3' (SEQ ID NO:3); reverse primer (R) 5'-AATATCCCATCACCATCTTTACTTGACC-3' (SEQ ID NO:4); hChAT, forward primer (F) 5'-GAGAAGACAGCCAACTGGGTG-3' (SEQ ID NO:5); reverse primer (R) 5'-CTCGTCCTCGTTGGAAGCCAT-3' (SEQ ID NO:6); hD1 dopamine receptor, forward primer (F) 5'-CTGTAACATCTGGGTGGCCT-3' (SEQ ID NO:7); reverse primer R) 5'-TGAGGCTGGAGTCACAGTTG-3' (SEQ ID NO:8); hD2 dopamine receptor, forward primer (F) 5'-TCCTGTCCTTCACCATCTCC-3' (SEQ ID NO:9); reverse primer (R) 5'-TGCAGACTTTCATGTCCTCG-3' (SEQ ID NO:10); G3PDH5 control, forward primer (F)

5'-ACCACAGTCCATGCCATCAC-3' (SEQ ID NO:11), reverse primer (R) 5'-TCCACCACCCTGTTGCTGTA-3' (SEQ ID NO:12)(G3PDH5, Clonetech). Each PCR reaction product was subjected to electrophoresis using a 6% trisborate polyacrylamide gel and the dried gel was exposed to a phosphorimage screen. The phosphorimage screen was analyzed using Molecular Analyst imaging software and the GS250 Molecular Imager (BioRad).

EXAMPLE 3

In Vivo Characterization of hNT Neurons hNT neurons were transplanted into host animals and tested for their ability to treat chemically induced models of Huntington's disease. Lesion and transplant procedures were performed stereotaxically under equithesin anesthesia (3.0 ml/kg, i.p.). In these experiments, male Sprague-Dawley rats (250–300 grams, Harlan, Indianapolis, Ind.) were injected with 1 $\mu$l/5 minutes of 300 nmole quinolinic acid (QA) into the left striatum (AP: 0.0, L: +2.4, from bregma; V: −5.6 from dura). Four weeks later, the lesion procedure was repeated at a second, more lateral site in the left striatum (AP: +0.5, L: +4.2, from bregma; V: −5.6 from dura) as described by Fricker et al. (Fricker et al., Brain Research Bulletin 41:409 [1996]). Two weeks following the introduction of the second lesion, animals were screened for successful lesion induction by testing for behavioral asymmetries in response to methamphetamine (5.0 mg/kg, i.p.) and apomorphine (1.0 mg/kg, s.c.), and for skilled motor use in the staircase test as described by Richard et al. and Montoya et al (Richards et al, Pharmacol. Biochem. Behav. 36:217 [1990]; and Montoya et al., J. Neuroscience Methods 36:219 [1991]).

Four weeks after establishment of behavioral deficits, lesioned animals received intrastriatal transplants of $0.5 \times 10^6$ hNT neurons, or $1.0 \times 10^6$ ED15 embryonic rat striatal cells in suspension, or vehicle injection in 3 $\mu$l volume into each of two sites (AP: 0.0 and 0.5, L: 2.9 and 3.7, from bregma, V: −6.5 to −3.5, from dura). To prevent rejection of the hNT neurons grafted into the animals, the animals were treated with cyclosporine (10 mg/kg/day, s.c.). Cyclosporine treatment started 48 hours prior to transplantation and was continued daily until the conclusion of the experiment. Animals were tested for methamphetamine and apomorphine-induced circling behavior at 4, 8, and 12 weeks post transplantation. At weeks 10 through 12 post-transplantation, animals were tested for skilled paw use in the staircase test.

EXAMPLE 4

Histochemical Assessment

Histochemical analysis was conducted to characterize lesions and transplanted cells. At 12 weeks after transplantation, animals were anesthetized with chloral hydrate (400 mg/kg) and intracardially perfused with cold heparinized saline followed by 4% paraformaldehyde. After cryopreservation in 305 sucrose, brains were frozen and 40 micrometer coronal sections cut on a cryostat. Sections were histochemically stained with cresyl violet (Nissl stain) for evaluation of the lesion and graft size. Immunohistochemical staining for the striatal cell marker, DARPP-32, was performed on transplants of both ED15 striatum and hNT neurons. Brain sections were incubated overnight at room temperature with monoclonal antibodies for DARPP-32 (1:10 000, a gift from Dr. Hugh Hemmings, Cornell Medical Center). The antibody-antigen interaction was visualized using biotinylated antimouse IgG (Calbiochem, La Jolla, Calif.) followed by peroxidase-diaminobenzidene using Vectastain kit (Vector Laboratories Inc., Burlingame, Calif.). The mass of the grafts was determined by scanning and analyzing sections with NIH-Image 1.57 image analysis software (Wayne Rasband, NIMH) on a Power Macintosh 8100/110 personal computer coupled to a slide scanner (Coolscan, Nikon).

EXAMPLE 5

Injections of Transplanted Cells

In these experiments, hNT neurons are transplanted into host animals. In one embodiment, injections are made with sterilized 10 $\mu$l Hamilton syringes having 23–27 gauge needles. The syringe, loaded with cells, are mounted directly into the head of a stereotaxic frame. The injection needle is lowered to predetermined coordinates through small burr holes in the cranium. 40–50 $\mu$l of suspension are deposited at the rate of about 1–2 $\mu$l/min and a further 2–5 minutes are allowed for diffusion prior to slow retraction of the needle. If desired, multiple deposits can be made along the same needle penetration. The injection may be performed manually or by an infusion pump. At the completion of surgery following retraction of the needle, the host is removed from the frame and the wound is sutured. Prophylactic antibiotics or immunosuppressive therapy may be administered as needed.

In other embodiments, hNT neurons are transplanted into human patients. Patients travel to the hospital the day prior to surgery. The patient is admitted and examined by a medical professional either the night before or the day of surgery. A series of standard preoperative tests and a loading dose of phenytoin are given. Patients are NPO (i.e., consuming nothing by mouth) after 10 p.m. the night before surgery.

During the surgery, a stereotactic surgical technique is performed using a CRW computed tomographic (CT) or magnetic resonance (MR) stereotaxic guide (Radionics, Burlington, Mass.). On the day of surgery, the stereotactic head ring is applied to the patient's head under local anesthesia. With the head ring in place, the patient undergoes CT or MR scanning. Baseline coordinates are established for the putamen. Typically, the long axis of putamen is 30–40 mm in length, and with a height suitable for 2 needle passes on each side. Local anesthesia is used on the skin of the forehead. Incisions 1 cm in length are made in the skin. Implantation is carried out through two 3 mm twist drill holes in the forehead on each side of the midline, one above the other, both below the hairline, and both above the frontal sinus. The patient is awake but sedated with intravenously administered drugs such as midazolam.

All patients are admitted to the recovery room for post-operative observations. Postoperative CT or MR scans are taken to show evidence of hemorrhage. A follow-up appointment for suture removal is made at four to five days after surgery. All patients receive broad-spectrum antibiotics for three days. Phenytoin is administered as prophylaxis against seizures for three days after surgery.

In some embodiments, the concentration of hNT neurons delivered to the patient is 100–$10^7$ cells/$\mu$l. In preferred embodiments, the concentration is $10^3$ to $10^5$ cells/$\mu$l. In particularly preferred embodiments, the concentration is $10^3$ to $10^4$ cells/$\mu$l, with a total of $10^7$ cells delivered to the patient. Concentrations and doses may vary depending on the particular patient, neurological disorder, and other relevant factors. One skilled in the art is capable of determining the therapeutically effective amount appropriate any given circumstances.

EXAMPLE 6

Cells Encapsulation

In these experiments, various embodiments for encapsulation of hNT neurons are described. hNT neurons can be encapsulated, to reduce host immune response to the transplantation. In one embodiment, the transformed cells are mixed with sodium alginate (i.e., a polyanionic seaweed extract) and extruded into a solution of divalent cations (e.g., calcium chloride) which complexes with the sodium alginate to form a gel, resulting in the formation of gelled beads or droplets containing the cells. The gel beads are incubated with a high molecular weight (e.g., MW 60–500×$10^3$) concentration (0.03–0.1% w/v) polyamino acid, such as poly-L-lysine, for a brief period of time (3–20 minutes) to form a membrane. The interior of the formed capsule is reliquified by treating with sodium citrate. The single membrane around the cells is highly permeable (MW cut-off of 200–400×$10^3$). The single membrane capsule containing the cell is incubated in a saline solution for 1–3 hours to allow entrapped sodium alginate to diffuse out of the capsule and expand the capsule to an equilibrium state. The resulting alginate-poor capsule is reacted with a low molecular weight polyamino acid (MW 10–30×$10^3$) such as poly-L-lysine or chitosan (deacetylated chitin; MW 240×$10^3$) to produce an interacted, less permeable membrane (MW cut-off of 40–80×$10^3$). The dual membrane encapsulated cells are then cultured for two to three weeks.

While reference has been made specifically to sodium alginate beads, it will be appreciated by those skilled in the art that any non-toxic water soluble substance that can be gelled to form a shape-retaining mass by a change in conditions in the medium in which it is placed may be employed. Such gelling material generally comprises several chemical moieties that are readily ionized to form anionic or cationic groups so that the surface layers can cross-link to form a permanent membrane when exposed to oppositely charged polymers. Most polysaccharide gums, both natural and synthetic, can be cross-linked by polymers containing positively charged reactive groups such as amino groups. The cross-linking biocompatible polymers that may be reacted with the sodium alginate gum include polylysine and other polyamino acids. The degree of permeability of the membrane formed may be controlled by careful selection of a polyamino acid having the desired molecular weight. While in preferred embodiments, poly-L-lysine is the preferred polymeric material, other embodiments utilize chitosan and polyacrylate material as the membrane. The molecular weights of the membranes typically vary from about $10^4$ to about $10^6$.

In one specific embodiment, hNT cells are removed from culture plates with 0.05% trypsin and 1 mM EDTA in Dulbecco's phosphate-buffered saline (PBS). The cells are suspended in PBS supplemented with $MgCl_2$, $CaCl_2$, 0.1% glucose, and 5% fetal bovine serum. Cells are collected by centrifugation, washed twice in the suspension solution as described above and centrifuged to a pellet.

The cell pellet remaining at the bottom of the centrifuge tube is resuspended in 5 ml of a 1.5% (w/v) sodium alginate solution (KELTONE LV by Kelco, Ltd., Chicago, Ill.). The alginate cell suspension is extruded into 50 ml of a 1.5% (w/v) $CaCl_2$ solution. Spherical droplets of the suspension are formed by an air jet-syringe pump droplet generator. With this apparatus, the cell-sodium-alginate suspension is extruded through a 22-gauge needle located inside a sheathed tube (3 mm I.D.) through which air flows at a controlled rate (9 L min). As liquid droplets are forced out of the end of the needle by the syringe pump (at 20 cc hr), the droplets are pulled off by the shear forces set up by the rapidly flowing air stream. The needle tip is kept 8 cm above the surface of the $CaCl_2$ solution surface to ensure that uniform, spherical gel droplets are formed with a diameter of about 300–1000 microns.

A sample of the gelled microbeads is examined for size and shape consistency using a dissecting microscope (Wild Heerbrugg Model M8) fitted with a calibrated eye-piece. After transferring the calcium alginate gel beads containing the immobilized cells to a 50 ml plastic centrifuge tube with a conical bottom, the beads are washed with 30 ml each of 0.1% (w/v) CHES and 1.1% (w/v) $CaCl_2$ solutions. The supernatant volume is reduced after each washing using a vacuum aspirator. A semi-permeable capsule membrane is formed by reacting the gel droplets with an aqueous 0.05% (w/v) PLL solution (M/v of PLL=22.000) for 8 minutes. After the addition of the PLL solution, the centrifuge tube is capped and manually rocked end-to-end for the duration of the reaction to keep the capsules from sticking together. The resultant microcapsules, 300–1000 microns in diameter, are washed with 30 ml each of 0.1% CHES and 1.1% $CaCl_2$ and with two 30 ml aliquots of isotonic saline. The encapsulated cells are contacted with 30 ml of 0.03% (w/v) sodium alginate solution for 4 minutes formed an outer layer on the capsules. The interior of the microcapsules is liquified with 30 ml of a 0.05M sodium citrate solution for six minutes. The microcapsules, 400–1400 microns in diameter, are washed several times in saline to remove excess citrate and then divided into five 1 ml aliquots. Each aliquot is incubated in 10 ml DMEM medium in a 25 $cm^3$ culture flask at 37° C.

EXAMPLE 7

Transfection of hNT Cells

In these embodiments, undifferentiated NT2 cells are transfected with a heterologous nucleic acid to provide differentiated hNT neurons with altered genetic functionality. Undifferentiated NT2 cells are transfected with 100 µg of expression vector and 10 µg of pSV2neo by lipofection using Lipofectin (Bethesda Research Laboratories). After 2 days in complete medium, the transfectants are selected with 200 µg/ml G418 (Gibco) for seven days. Cells extracts are taken and assayed for the presence of the expression product by Western blot using standard procedures. Cells that are positive for the desired expression product are maintained and differentiated as described in Example 1.

EXAMPLE 8

Behavioral Assays

These experiments provide examples of behavioral assays for identifying neural dysfunction in animals.
I. The Staircase Test
The staircase test provides a measure of independent forelimb reaching and grasping abilities in test animals as described by Montoya et al. (See e.g., Montoya et al., supra), incorporated herein by reference. Briefly, a test apparatus was prepared that takes advantage of the fact that rats readily enter narrow spaces in order to gain access to food. The apparatus consisted of a plexiglass box, 285 mm long by 90 mm high by 60 mm wide. A central wooded platform ran along two thirds of the length with a 16.5 mm wide trough on either side. The top surface of the platform was 27 mm wide, and overhung the sides so as to prevent animals from simply scraping food pellets up the side of the platform. A removable double staircase was inserted into the end of the box, so as to be positioned in the troughs on either side of the central platform. Each step of the 7-step staircase contained a small 3 mm deep well into which one or more food pellets were placed. A barrier across the end wall prevented the rat from escaping out of the end of the box. At the other end of the box, the floor was cut away and provided easy access for entry and removal of the animal at the beginning and end of the session.

The double staircase was removed from the box and food pellets were placed into each well. Food-deprived rats were placed into the test boxes and the double staircase was inserted. Tests were conducted for 15 minutes. The staircase was removed and the number of pellets remaining in each well on the two sides was counted. The total number of pellets retrieved on each side was calculated. Typically, the data from each rat are combined over several days to increase the power of the test. In some embodiments, just one side of the staircase was baited.

Prior to surgery, animals received a single test to habituate them to the apparatus, by the end of which all animals reached consistently on both sides for food rewards. They received three further tests on the following 3 days, which provided preoperative baseline levels of performance.

II. Circling Behavior

Rats were trained to turn for water reinforcement as described by Richards et al. (Richards et al., J. Neural Trans. & Plast. 4:157 [1993]), herein incorporated by reference. After the animals were given lesions, they showed deficits in trained turning. The rats were deprived of water for 23.5 hours during training and testing.

Turning was monitored automatically with four identical rotometers connected to microcomputers. These rotometers have previously been described in detail by Richards et al. (Richards et al., Physiol. Behav. 47:1083 [1990]), herein incorporated by reference. Briefly, the rotometers consisted of a shaft which was mounted in a bearing and attached to the animals by a length of model aircraft cable and a harness. A pointer fitted to the shaft interrupted beams from infrared-light-emitting diodes falling on an array of photo transistors as the animals turned. Output from the photo transistors was received by a computer which monitored the rats' turning movements and rewarded the rats for turns in the correct direction. The rats were confined by clear acrylic tubes (diameter=20 cm; height=38 cm) placed on a flat grid floor. A liquid dispenser (model 80201, Lafayetter Instrument Company) was used to provide 0.05 ml water drops. The rotometers were placed inside sound-attenuating chambers made of 5 cm thick Styrofoam. The sound-attenuating chambers were equipped with a fan and house light.

The rats were trained to rotate in both left and right directions for water reinforcement. The animals were trained for 3 weeks (5 days a week) before receiving lesions. The pre-lesion baseline data used for analysis were taken from the last two days of the initial training period Approximately 2 weeks after lesion surgery, the animals were tested for drug-induced rotation. Then the rats were water deprived and retrained for one week in the trained turning task. The post-lesion turning data used for analysis were taken from the last two days of the second training period.

After transplantation, the rats were rested with full access to water and then water deprived and trained for two weeks on the conditioned rotation procedure. This regimen was repeated multiple times. Data from the last two days of each two week conditioned rotation test period were used for data analysis.

From the above, it is clear that the present invention provides methods and compositions for the treatment of neurological diseases such as Huntington's disease. In addition, it is clear that the present invention provides useful animal models for the development of additional treatment regimens for neurological diseases.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, medicine, neurobiology, and molecular biology or related fields are intended to be within the scope of the following claims.

We claim:

1. A method of improving the motor skills of an individual with Huntington's disease comprising providing a plurality of hNT neurons into the corpus striatum of an individual with Huntington's disease such that the motor skills of the individual with Huntington's disease are improved.

2. The method of claim 1, wherein the individual is a human.

* * * * *